(12) United States Patent
Chung (10) Patent No.: US 11,287,318 B2
(45) Date of Patent: Mar. 29, 2022

(54) COMPACT OCT SPECTROMETER SUITABLE FOR MOBILE ENVIRONMENT

(71) Applicant: PHILOPHOS, INC., Seongnam-si (KR)

(72) Inventor: Jung-Ho Chung, Yongin-si (KR)

(73) Assignee: PHILOPHOS, INC., Seongnam-si (KR)

( * ) Notice: Subject to any disclaimer, the term of this patent is extended or adjusted under 35 U.S.C. 154(b) by 0 days.

(21) Appl. No.: 17/110,998

(22) Filed: Dec. 3, 2020

(65) Prior Publication Data

US 2021/0116301 A1 Apr. 22, 2021

Related U.S. Application Data

(63) Continuation of application No. PCT/KR2019/006762, filed on Jun. 4, 2019.

(30) Foreign Application Priority Data

Jun. 5, 2018 (KR) .................. 10-2018-0064969
Jul. 24, 2018 (KR) .................. 10-2018-0086004

(51) Int. Cl.
  *G01B 11/02* (2006.01)
  *G01J 3/02* (2006.01)
  (Continued)

(52) U.S. Cl.
  CPC .......... *G01J 3/0256* (2013.01); *A61B 3/0025* (2013.01); *A61B 3/102* (2013.01);
  (Continued)

(58) Field of Classification Search
  CPC ...... G01J 3/0256; G01J 3/0272; G01J 3/4412; A61B 3/0025; A61B 3/102;
  (Continued)

(56) References Cited

U.S. PATENT DOCUMENTS

2017/0176168 A1* 6/2017 Brown ............... G01B 9/02054
2017/0184453 A1* 6/2017 Wang ........................ G01J 3/36

FOREIGN PATENT DOCUMENTS

EP 3301894 A1 * 4/2018 ............. G01B 11/14
JP 201356171 A 3/2013
(Continued)

OTHER PUBLICATIONS

"Optical Sensor-On-Chip ICs Simplify Handheld Spectrometer Design", Digi-key electronics, Jun. 28, 2017 (https://www.digikey.com/en/articles/optical-sensor-on-chip-ics-simplify-handheld-spectrometer-design) (Year: 2017).*

(Continued)

*Primary Examiner* — Tarifur R Chowdhury
*Assistant Examiner* — Jonathon Cook
(74) *Attorney, Agent, or Firm* — Dinsmore & Shohl LLP; Yongsok Choi, Esq.

(57) ABSTRACT

A compact handheld optical coherence tomography (OCT) spectrometer according to an embodiment of the present disclosure includes: a spectrometer optical module; a sensor board coupled to one side of the spectrometer optical module and including a sensor that converts light received from the spectrometer optical module into an electrical signal; and a connector configured to supply, to the sensor board, a control signal and a power signal received from another circuit outside the spectrometer and to transmit a signal received from the sensor board to another external circuit, and the sensor board is packaged with the spectrometer optical module, and the sensor is not indented but is formed to protrude from the surface of the sensor board, and a light receiving portion of the sensor is configured to face the inside of the packaged component and collect light from the spectrometer optical module.

13 Claims, 7 Drawing Sheets

(51) Int. Cl.
*A61B 3/00* (2006.01)
*A61B 3/10* (2006.01)
*G01B 9/02091* (2022.01)
*G01J 3/44* (2006.01)

(52) U.S. Cl.
CPC ........ *G01B 9/02091* (2013.01); *G01J 3/0272* (2013.01); *G01J 3/4412* (2013.01); *A61B 2560/0431* (2013.01); *A61B 2560/0462* (2013.01)

(58) Field of Classification Search
CPC .... A61B 2560/0431; A61B 2560/0462; G01B 9/02091
See application file for complete search history.

(56) References Cited

FOREIGN PATENT DOCUMENTS

| | | |
|---|---|---|
| KR | 1020130026502 A | 3/2013 |
| KR | 1020140102034 A | 8/2014 |
| KR | 1020160138124 A | 12/2016 |
| KR | 101765824 B1 | 8/2017 |
| KR | 1020180032482 A | 3/2018 |
| WO | WO-2015082564 A1 * | 6/2015 ................ G01J 3/44 |

OTHER PUBLICATIONS

International Search Report of PCT/KR2019/006762 dated Sep. 3, 2019.

* cited by examiner

*FIG. 1*

PRIOR ART

FIG. 2A

PRIOR ART

FIG. 2B

PRIOR ART

COMPACT OCT SPECTROMETER SUITABLE FOR MOBILE ENVIRONMENT

CROSS-REFERENCE TO RELATED APPLICATION

This application is a continuation of International Application No. PCT/KR2019/006762 filed on Jun. 4, 2019, which claims priority to Korean Patent Application No. 10-2018-0064969 filed on Jun. 5, 2018 and Korean Patent Application No. 10-2018-0086004 filed on Jul. 24, 2018, the entire contents of which are herein incorporated by reference.

TECHNICAL FIELD

The present disclosure relates to a technology for implementing a compact optical coherence tomography (OCT) spectrometer suitable for a mobile environment.

BACKGROUND

OCT is an advanced medical diagnostic technology that enables the inside of a biological tissue to be observed by using light and has been used in the fields of ophthalmology, cardiovascular medicine and the like. The OCT can be implemented by such configurations as time domain, spectral domain and swept source. Particularly, the spectral domain OCT system ensures a certain level of performance and requires less manufacturing cost and thus has received a lot of attention.

Figure 1:
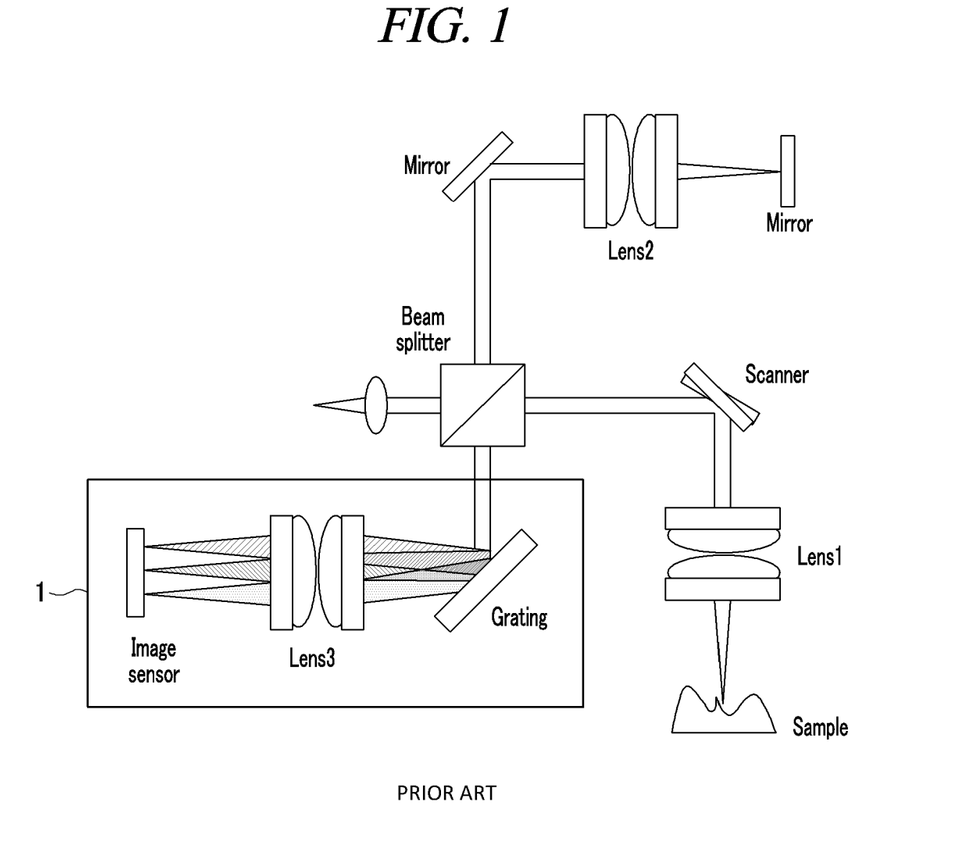
FIG. 1 is a conceptual diagram of a conventional spectral domain OCT system.

FIG. 1 is a conceptual diagram of a conventional spectral domain OCT system.

Referring to FIG. 1, a spectrometer 1 is an essential component of a spectral domain OCT system and is configured to spectrally disperse reference light and sample light, which has back-scattered from a biological tissue, and then, to make a sensor detect the interference signal, enabling a structural signal of the inside of the biological tissue to be acquired.

Also, OCT has expanded its market mainly in the fields of ophthalmology and cardiovascular medicine but has not been widely applied to other diagnostic fields since it was invented in 1991. The main reasons for this include the facts that the OCT system is expensive up to one hundred million won, that it is usually configured into a desktop or cart structure requiring a certain degree of installation space, and that it requires high usage fees and medical insurance fees.

Therefore, if the OCT system becomes compact in size and low in price, it can be widely applied to various diagnostic fields. To this end, the spectrometer needs to be compact in size and low in price.

To accurately image the internal cross section of a biological tissue by the OCT system using the spectrometer 1, artificial noises need to be minimized. Conventionally, part of light is reflected in the spectrometer due to a cover window of a sensor that converts light into an electrical signal, and, thus, when OCT cross-section images are displayed, artificial horizontal line noises are generated.

However, the cover window is manufactured as a single package with the sensor and is difficult to arbitrarily remove. Further, in such a single package, the sensor is usually indented from the surface, which hinders miniaturization of a spectrometer.

Figure 2A:
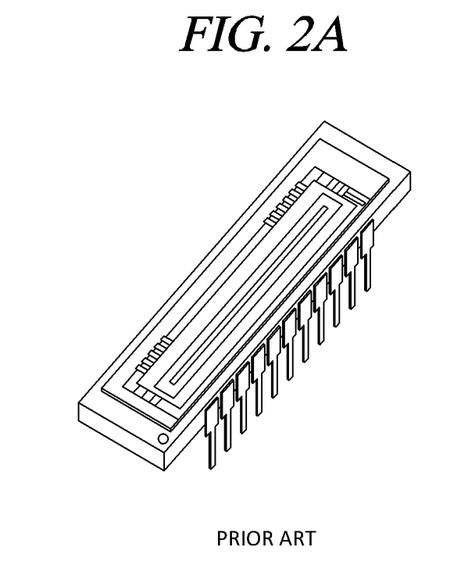
FIG. 2A illustrates a sensor used in a conventional spectrometer.
Figure 2B:
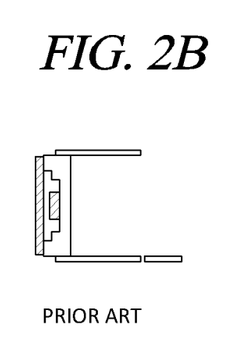
FIG. 2B illustrates a sensor used in a conventional spectrometer.

FIGS. 2A and 2B illustrates a sensor used in the conventional spectrometer 1.

FIG. 2A shows the top surface of the sensor and FIG. 2B shows the side surface of the sensor.

It can be seen from FIG. 2A that the conventional sensor is equipped with a cover window on its surface and an actual detection region is indented from the surface and this can be seen from FIG. 2B.

Further, the conventional OCT spectrometer 1 does not take into consideration a handheld or mobile environment and thus is equipped with a power supply circuit for supplying power to a sensor circuit of the spectrometer 1 and a connector. Therefore, the spectrometer 1 needs to be connected to a separate power adaptor, which is an obstacle to miniaturization of a spectrometer.

Furthermore, in a sensor board of the spectrometer 1, one needs to take into thorough consideration the sensitivity of a sensor. If the sensitivity of the sensor is high, fewer photons can generate a sufficient current, but if the sensitivity of the sensor is low, a high-power light source is needed. This structure is not suitable for a handheld or mobile OCT requiring low power consumption. Therefore, the spectrometer 1 using a sensor with high sensitivity needs to be implemented.

When the sensitivity of the sensor is taken into consideration, the full well capacity of the sensor also needs to be considered. When light reaches the sensor, photons generate electrons, and in this case, the number of electrons accumulated in each pixel for an integration time till a saturation level is the full well capacity. No matter how good the sensitivity of the sensor is, if the full well capacity is low, the pixel is immediately saturated, and, thus, the intensity of an incident light signal is limited. Therefore, an OCT spectrometer suitable for a mobile environment needs to be equipped with a sensor with high sensitivity as well as high full well capacity.

SUMMARY

Problems to be Solved by the Invention

The present disclosure provides a compact spectrometer 1 suitable for a battery-powered handheld or mobile OCT device.

Means for Solving the Problems

To solve the above-described problem, according to an embodiment of the present disclosure, a compact handheld optical coherence tomography (OCT) spectrometer includes: a spectrometer optical module; a sensor board coupled to one side of the spectrometer optical module and equipped with a sensor that converts light received from the spectrometer optical module into an electrical signal; and a connector configured to supply, to the sensor board, a control signal and a power signal received from another circuit outside the spectrometer and to transmit a signal received from the sensor board to another external circuit, and the sensor board is packaged with the spectrometer optical module, and the sensor is formed to protrude from the surface of the sensor board, and a light receiving portion of the sensor is configured to face the inside of the packaged components and collect light from the spectrometer optical module.

Also, the sensor itself may be manufactured to be embedded in the sensor board without going through its own packaging process.

Further, a cover glass may not be provided on top of the light receiving portion of the sensor.

Furthermore, each of a plurality of pixels forming the sensor may have a width of less than 10 μm.

Moreover, the sensor may be configured as a low-power circuit to operate with a predetermined input power.

Besides, the deterioration of spectral performance may be minimized by designing the size of the focus of each wavelength component of a light signal received by the sensor to be smaller than the width of the pixel.

Further, the sensor board may be equipped with a voltage conversion unit, so that if the sensor board does not receive a predetermined voltage from the connector, the voltage conversion unit may convert a power signal transmitted from the connector into another voltage level required for power supply.

Furthermore, the sensor board may further include an analog-to-digital converter that converts an analog signal received from the sensor into a digital signal and transmits the digital signal to the connector, and the analog-to-digital converter has a voltage range of the input analog signal level from a noise floor to a voltage level corresponding to a full well capacity of the sensor, and the full well capacity may refer to the maximum number of electrons accumulated for a predetermined period of time in each pixel inside the sensor after the pixel receives light.

Moreover, the connector may transmit the digital signal generated by the analog-to-digital converter to a main board outside the spectrometer.

Besides, the spectrometer may further include a correction module configured to perform the correction to an electrical signal value measured from each pixel of the sensor, and the correction module may perform the correction to reduce differences in electrical signal values among the pixels caused by unequal photoelectric conversion characteristic values in the pixels and to reduce differences in noise floor characteristic values among the pixels when no light is incoming.

Also, the correction module may perform the correction by subtracting the factors reflecting different offset values of respective pixels from the electrical signal values measured from the respective pixels and then dividing the resulting values by the factors reflecting different gain values of the respective pixels for identical input light levels.

Effects of the Invention

According to an embodiment of the present disclosure, it is possible to implement a compact spectrometer 1 suitable for a battery-powered handheld or mobile OCT device.

According to the present disclosure, it is possible to reduce the size and price of a spectral domain OCT system by reducing the size of the spectrometer 1, minimizing power consumption and implementing a sensor and an optical system as a single package.

Accordingly, it is possible to maximize the penetration rate of OCT, which has been limited so far, and generalize diagnostics based on the OCT. thus, expecting the expansion of medical insurance fees also.

In addition, the handheld or mobile OCT system can be positioned as a point-of-care (POC) device, which enables doctors to visit patients even in areas with poor access to hospitals and expand medical benefits with advanced diagnostic devices.

DETAILED DESCRIPTION

Hereafter, embodiments will be described in detail with reference to the accompanying drawings so that the present disclosure may be readily implemented by a person with ordinary skills in the art. However, it is to be noted that the present disclosure is not limited to the embodiments but can be embodied in various other ways. In the drawings, the parts irrelevant to the description are omitted for the simplicity of explanation, and like reference numerals denote like parts throughout the whole document.

Throughout the whole document, the term "connected to" or "coupled to" that is used to designate a connection or coupling of one element to another element includes both a case that an element is "directly connected or coupled to" another element and a case that an element is "electronically connected or coupled to" another element via the third element. Further, it is to be understood that the term "comprises or includes" and/or "comprising or including" used in the document means that, in addition to the described components, steps, operations and/or elements, one or more other components, steps, operations and/or existence or addition of elements are not excluded unless the context dictates otherwise and is not intended to preclude the possibility that one or more other features, numbers, steps, operations, components, parts, or combinations thereof may exist or may be added.

Throughout the whole document, the term "unit" includes a unit implemented by hardware, a unit implemented by software, and a unit implemented by both of them. One unit may be implemented by two or more pieces of hardware, and two or more units may be implemented by one piece of hardware. However, "the unit" is not limited to the software or the hardware, and "the unit" may be saved in an addressable storage medium or may be configured to run one or more processors. Accordingly, "the unit" may include, for example, software, object-oriented software, classes, tasks, processes, functions, attributes, procedures, sub-routines, segments of program codes, drivers, firmware, micro codes, circuits, data, database, data structures, tables, arrays, variables and the like. The components and functions in "a unit" can be combined with each other or can be divided up into additional components and "the units". Further, the components and "the units" may be configured to run one or more CPUs in a device or a secure multimedia card.

The following exemplary embodiments are provided only for understanding of the present disclosure but not intended to limit the scope of the right of the present disclosure. Therefore, the inventions that perform the same functions in the same scope as the present disclosure are also included in the scope of the right of the present disclosure.

Figure 3:
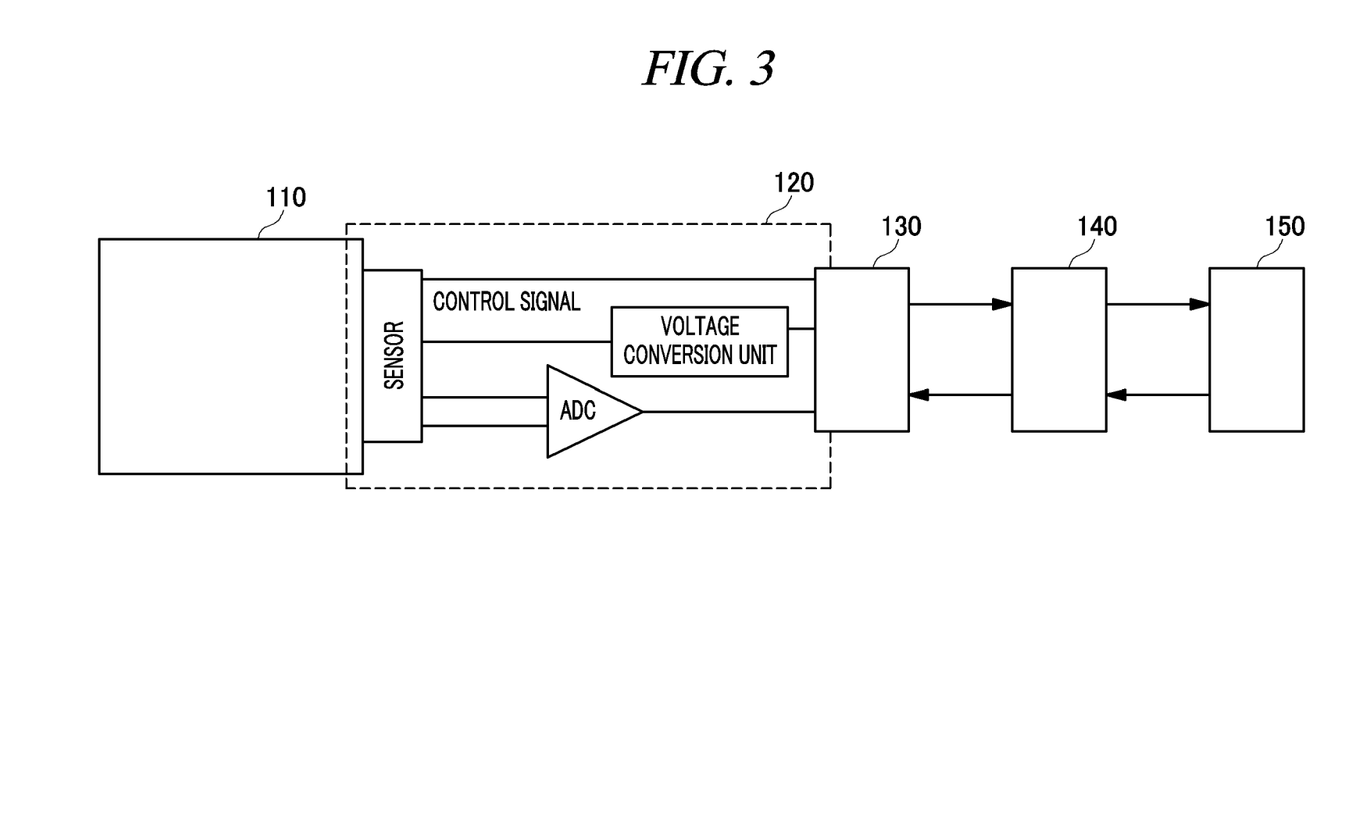
FIG. 3 illustrates the configuration of a compact OCT spectrometer and a subsequent signal processing stages according to an embodiment of the present disclosure.

FIG. 3 illustrates the configuration of a compact OCT spectrometer 1 and a subsequent signal processing stages according to an embodiment of the present disclosure.

Referring to FIG. 3, the spectrometer 1 may include a spectrometer optical module 110, a sensor board 120 and a connector 130 which may be connected to a main board 140 and a power supply device 150 of the OCT spectrometer 1.

The spectrometer optical module 110 is comprised of lenses, mirrors, and the like within the spectrometer 1 and functions to guide a light signal returning from a measuring target to get dispersed spectrally and appropriately reach a sensor.

Figure 4A:
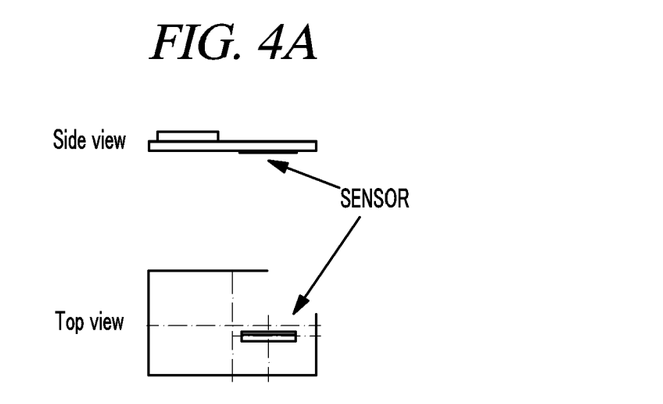
FIG. 4A illustrates an example of a sensor according to an embodiment of the present disclosure.
Figure 4B:
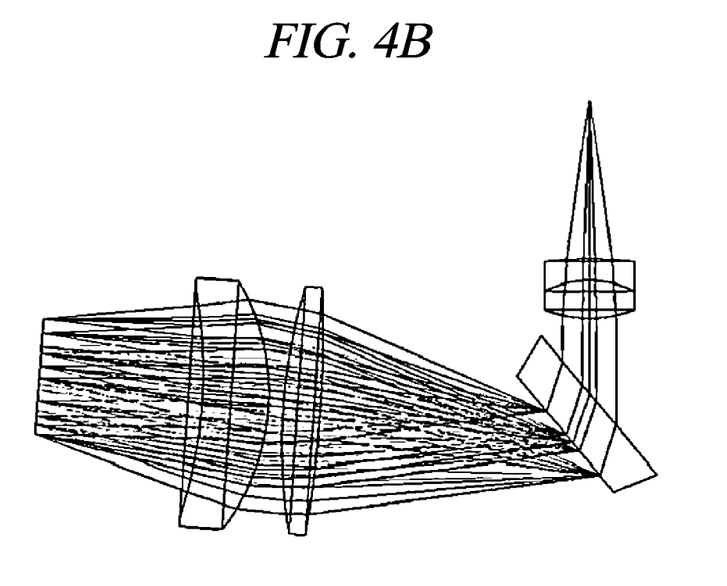
FIG. 4B illustrates an example of a spectrometer according to an embodiment of the present disclosure.

In the present disclosure, optical components used in the spectrometer optical module 110 may be reduced in size or integrated to miniaturize the spectrometer 1, and an example thereof can be seen from FIG. 4B.

The sensor board 120 is coupled to one side of the spectrometer optical module 110 and includes a sensor that converts a light signal received from the spectrometer optical module 110 into an electrical signal, and transmits the converted signal to the outside through the connector 130.

Further, the sensor board 120 is packaged with the spectrometer optical module 110, and the sensor is not indented but formed to protrude from the surface of the sensor board 120 (i.e., so as to be exposed to the outside out of the surface of the sensor board), and the light receiving portion of the sensor is configured to face the inside of the packaged spectrometer and collect light from the spectrometer optical module 110.

Here, the sensor itself is mounted on the sensor board 120 without going through its own separate packaging process and then packaged with the spectrometer optical module 110. Therefore, a cover glass which has been provided on top of a conventional sensor so as to protect the sensor can be omitted. In contrast, if a cover glass is provided as in the conventional technology, it may cause a noise when an OCT image is generated.

The sensor board 120 may further include an analog-to-digital converter (ADC) that converts an analog signal received from the sensor into a digital signal.

When the analog-to-digital converter converts an analog signal into a digital signal, the minimum output of the digital signal needs to be set lower than a value corresponding to the noise floor of the sensor and the maximum output needs to be set higher than a voltage corresponding to the full well capacity of the sensor.

Here, the full well capacity refers to the number of electrons generated for a predetermined period of time up to the saturation level by each pixel inside the sensor after the pixel receives light.

Figure 6A:
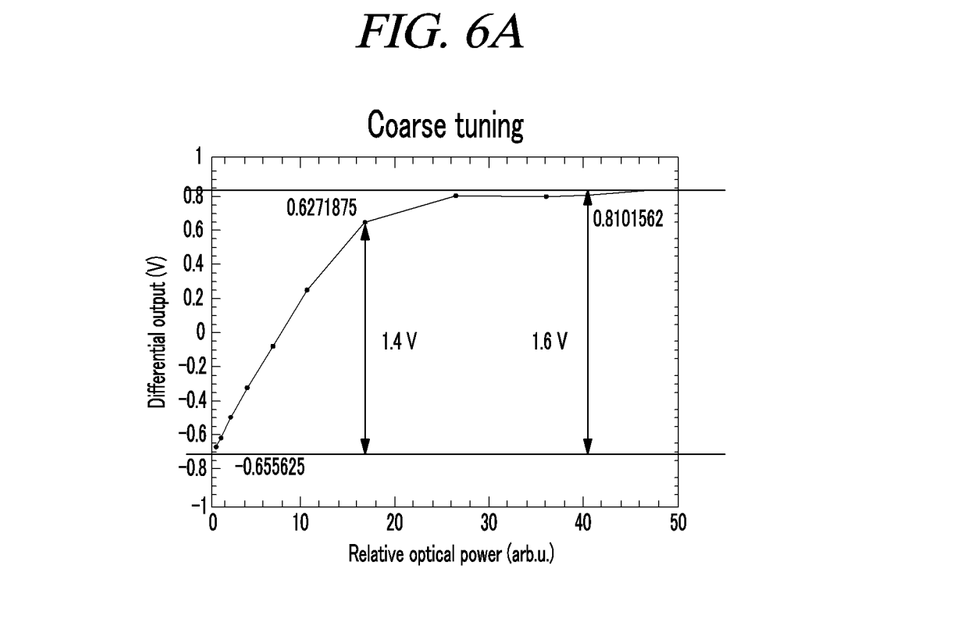
FIG. 6A provides a graph showing an exemplary process of securing the linearity of output from a sensor board according to an embodiment of the present disclosure.

More specifically, in general, when the intensity of an input light signal increases, if an output analog signal is higher than the full well capacity of the sensor, electrons are further saturated and the linearity of the output signal to the input light signal is broken as shown in graph of FIG. 6A. That is, it is desirable that when the intensity of input light increases, an output voltage should be generated so as to maintain its linearity as shown in graph of FIG. 6B, but in general, the linearity can be broken. Therefore, it is desirable that analog-to-digital conversion should be performed within a range in which the linearity between the intensity of input light and an output electrical signal can be maintained by using a sensor with high full well capacity.

Here, even when the sensor has good sensitivity and the intensity of an electrical signal generated in response to a certain input light signal is high, if the full well capacity is low, the acquired electrical signal may not accurately reflect the light signal.

Therefore, in the present disclosure, the voltage set for the analog-to-digital converter has such range that it can mainly digitize the input voltages from the level corresponding to the noise floor to the level corresponding to the full well capacity (i.e., within a voltage range in which linearity can be maintained).

A power source for the sensor board 120 may be implemented to be provided by using a signal processing cable, such as a USB cable for charging, rather than a separate power adaptor, and, thus, the spectrometer 1 can be compact in size.

Here, if power sources of various voltages cannot be applied from the outside, a voltage conversion unit provided inside the sensor board 120 converts a voltage signal received from the connector 130 through the signal processing cable into another voltage required for the power source to apply to the sensor, the analog-to-digital converter and the like.

Further, in another embodiment, an additional circuit unit for noise reduction or electric shock prevention may be provided in the sensor board 120.

In yet another embodiment, the sensor board 120 may be implemented as a single board or may be implemented in two or more boards by dividing its functions.

The connector 130 is connected to the sensor board 120 and configured to supply a signal to the sensor board 120 based on a control signal and a power signal received from another circuit (the main board 140). Further, the connector 130 transmits a signal received from the sensor board 120 to the main board 140 and is supplied with the power source from an OCT main body including the main board 140.

The main board 140 refers to a circuit board included in the OCT main body connected to the spectrometer 1 of the present disclosure. A control signal generated from the main board 140 of the OCT main body and the power source generated from the power supply device 150 are transmitted through the connector 130, and the main board 140 receives a signal acquired accordingly from the spectrometer.

Therefore, the digital signal generated from the analog-to-digital converter of the sensor board 120 is transmitted to the main board 140 through the connector 130.

The power supply device 150 may be connected to the main board 140 to transmit the power source to the OCT main body and the spectrometer 1. Here, in the present disclosure, the power supply device 150 may be implemented as a removable or rechargeable battery, since the spectrometer 1 is provided in a compact portable OCT device.

The spectrometer 1 according to the present disclosure needs to be supported by a mechanical design for fastening parts, packaging and absorbing shock in order to withstand drops in consideration of a handheld or mobile environment.

FIGS. 4A and 4B illustrate an example of a sensor and the spectrometer optical module 110 according to an embodiment of the present disclosure.

FIG. 4A shows an implementation example of the sensor and FIG. 4B shows an example of the spectrometer optical module 110.

Referring to FIG. 4A, the sensor is not packaged alone and not equipped with a cover window in order to reduce an artificial noise. In order to enable compact packaging of the spectrometer 1, the surface of the sensor from which the cover window is removed protrudes from the sensor board 120 to the outside.

Here, each pixel forming the sensor is manufactured to have a small width of less than 10 μm, and, thus, when the sensor is manufactured as a single package with the spectrometer optical module 110 of the spectrometer 1, the overall size can be reduced. Further, the sensor needs to be configured as a low-power circuit to operate with low power consumption.

Referring to FIG. 4A, the electronic circuit board including the sensor has the detection region of the sensor protrude from the surface and there is no cover window and is combined with the left end of the spectrometer optical module as depicted in FIG. 4B so that the overall spectrometer 1 can be compact in size.

The surface of the protruding sensor can be used in a geometric optical system composed of lenses, a grating and the like as shown in FIG. 4B, and is suitable for integrated optics in which optical components are implemented as waveguides in a plane through a semiconductor processes for further miniaturization.

Further, one of the metrics for evaluating the performance of the OCT system is the optical detection sensitivity or optical dynamic range.

The optical detection sensitivity refers to the signal-to-noise ratio (SNR) assuming that fully reflective mirror is located at a sample position. Various noise components include shot noise, thermal noise, and relative intensity noise (RIN).

Therefore, as for a biological tissue with high scattering and absorption, the system can be driven in a shot-noise limited environment where a shot noise is extremely high.

In this case, as the integration time of the sensor increases, the optical detection sensitivity increases, but the operating speed of the spectrometer decreases. Therefore, an appropriate compromise needs to be found.

Here, the optical detection sensitivity deteriorates as a light signal go deep into the biological tissue and returns. The degree of deterioration is related to the ratio of the size of the focus of each wavelength component formed on each pixel of the sensor to the width of each pixel. In the present disclosure, the size of the focus is designed to be smaller than the pixel width to minimize the deterioration of the optical detection sensitivity.

In most multi-pixel sensors, the pixels are not uniform in characteristics depending on semiconductor processes and thus have photo response non-uniformity (PRNU) and dark signal non-uniformity (DSNU). The former is slight variations in the amount of current generated for an identical amount of input photons, and the latter is slight variations when light is not incoming. That is, the PRNU is the factor related to the gain of each pixel, and the DSNU is the factor related to the offset value of each pixel.

In the present disclosure, the spectrometer 1 further includes a correction module for performing the correction on an electrical signal value measured from each pixel of the sensor, and the correction module performs the correction to reduce the differences in electrical signal values of the pixels caused by different photoelectric conversion characteristic values in the pixels and reduce differences in noise floor characteristic values among the pixels when light is not incoming.

In this case, the correction module subtracts the factors reflecting differences in the offset values of respective pixels from the electrical signal values measured from the respective pixels and then dividing the resulting values by the factors reflecting different gain values of the respective pixels for identical input light levels.

Therefore, a measured value of each pixel can be accurate only after corrected by using the PRNU and DSNU values for each pixel that have been previously analyzed. That is, the signal corrected as in the following Equation 1 is obtained.

$$S_{cal}(i) = \frac{S_{meas}(i) - DSNU(i)}{PRNU(i)} \qquad \text{[Equation 1]}$$

Figure 5:
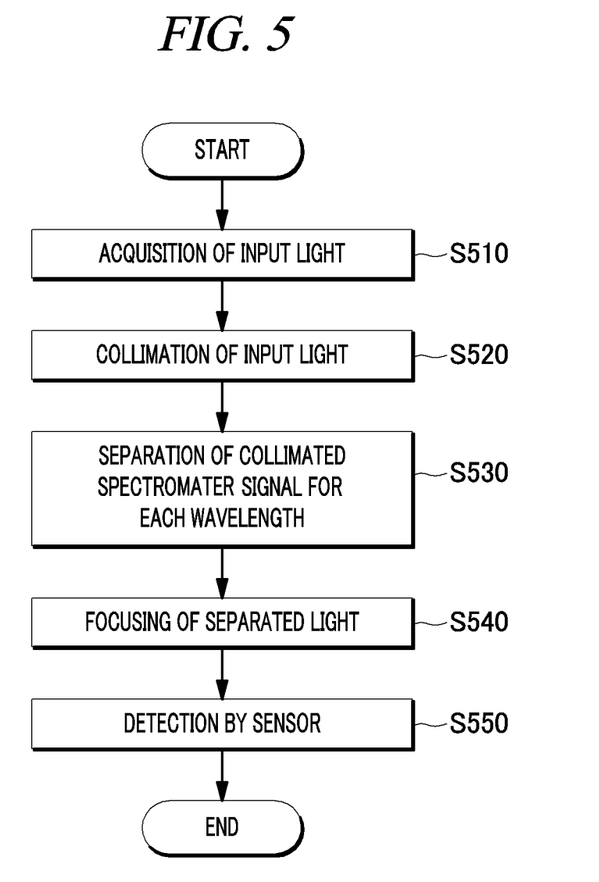
FIG. 5 is a flowchart showing processes of processing light incident to a spectrometer optical module according to an embodiment of the present disclosure.

FIG. 5 is a flowchart showing processes of processing light incident to the spectrometer optical module 110 according to an embodiment of the present disclosure.

Referring to FIG. 5, first, incident light is acquired by the spectrometer optical module 110 (S510).

The incident light acquired through the process S510 is subjected to collimation through a lens provided in the spectrometer optical module 110 (S520).

The collimated spectrometer signal is separated according to their wavelength components (S530), and the separated spectrometer signal is focused through lenses provided in the spectrometer optical module 110 (S540).

Finally, the spectrally dispersed signal, which has been focused through the process S540, is detected by the sensor provided in the sensor board 120 (S550).

Figure 6B:
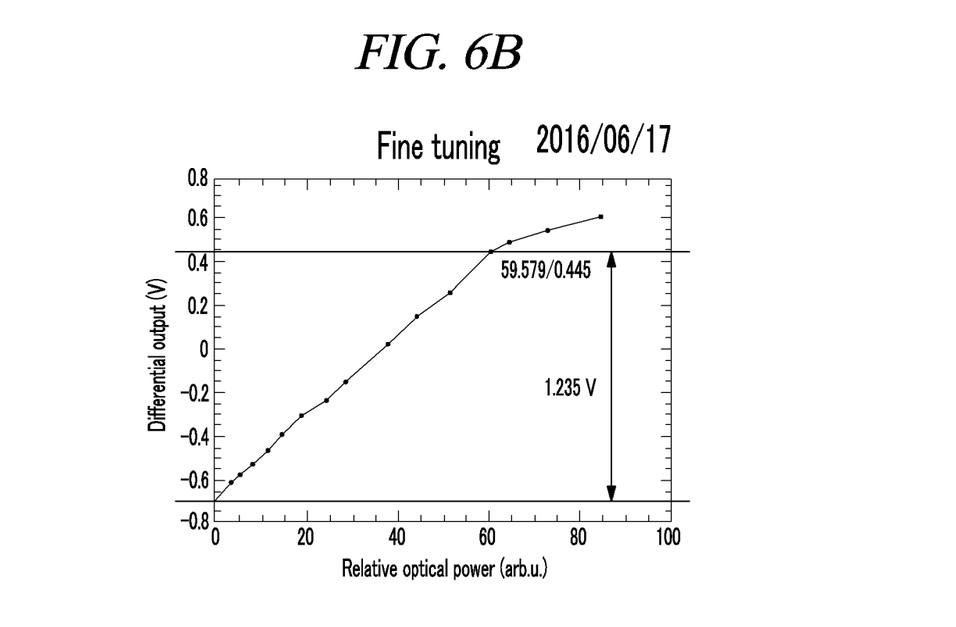
FIG. 6B provides a graph showing an exemplary process of securing the linearity of output from a sensor board according to an embodiment of the present disclosure.

FIGS. 6A and 6B provides the graphs showing an example of a process of securing the linearity of the output from the sensor board 120 according to an exemplary embodiment of the present disclosure.

The two graphs of FIGS. 6A and 6B are related to the degree of saturation versus the light signal. FIG. 6A shows an output signal (electrical signal value) of a typical spectrometer, and FIG. 6B shows an output signal (electrical signal value) of an ideal spectrometer.

First, referring to FIG. 6A, even if a light signal incident to a particular pixel increases linearly, an output value (electrical signal value) at that pixel may increase nonlinearly as shown in FIG. 6A. In such a case, if the output value is used as it is, an inaccurate output result is acquired from the spectrometer.

Therefore, when the nonlinear output value is corrected to a linear value using a predetermined algorithm, a linear output value as shown in FIG. 6B can be acquired. Thus, an accurate output result can be acquired from the spectrometer.

Here, in a predetermined algorithm, for example, a curve in a region where the output value relative to the input light signal is linear is extrapolated, an ideal linear output value in a nonlinear region is derived, a lookup table of the ideal linear output value for a nonlinear output value actually measured from a specific input light signal intensity is pre-stored, and then, if the spectrometer is actually operated and a nonlinear output value is received, the previously stored linear output value is retrieved from the lookup table and provided instead of the nonlinear output value. As another example, a function including the nonlinear state may be derived by such methods as curve fitting and then, a function for converting the nonlinear state into a linear state may be calculated and applied.

Such compensation can also be added to the PRNU and DSNU, and, thus, it is possible to increase the accuracy of resulting values to be acquired through the spectrometer.

In addition, a crosstalk compensation algorithm which can be applied to a conventional spectrometer may also be included. The crosstalk means that a sensor mounted inside the spectrometer is generally arranged in a one-dimensional form in which a light signal to be detected only within a single pixel leaks to adjacent pixels and is measured because of non-ideal operational characteristics of the sensor. Therefore, in a situation where a light signal is supposed to be incident to only one pixel, if electrical signal values of several adjacent pixels (about 1 to 3 pixels on a single side) are measured and then extended to all the pixels, a matrix equation is produced showing how an electrical signal value supposed to be measured from only one pixel in an ideal state is actually measured. Here, an electrical signal value measured from a pixel is corrected so as to correspond to an ideal electrical signal value by calculating an inverse matrix of the produced matrix equation.

Figure 7:
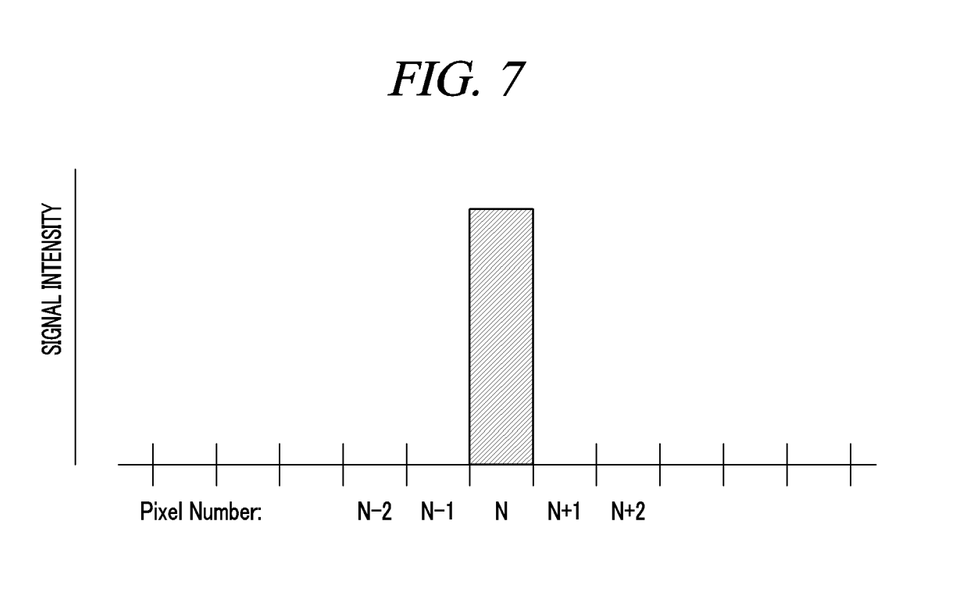
FIG. 7 depicts an exemplary graph showing the shape of a light signal shining on a pixel according to an embodiment of the present disclosure.
Figure 8:
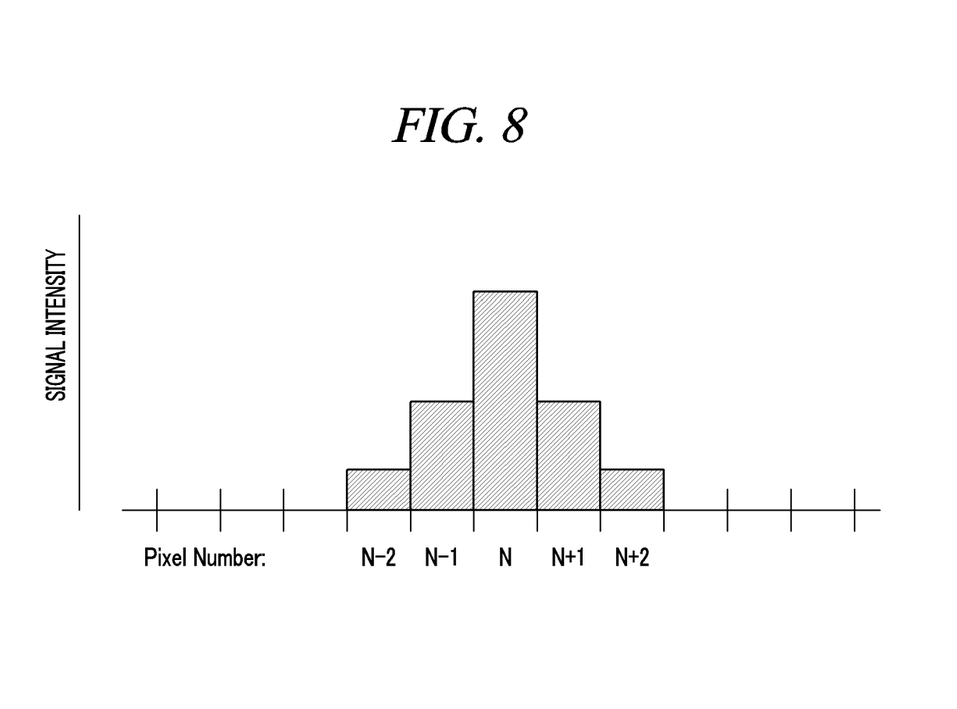
FIG. 8 depicts an exemplary graph showing the shape of a light signal shining on a pixel according to an embodiment of the present disclosure.

FIG. 7 and FIG. 8 are exemplary graphs showing the shape of a light signal incident based on a single pixel according to an embodiment of the present disclosure.

Referring to FIG. 7, in the ideal situation, if there is no crosstalk to the light signal, a signal is measured from only one pixel as shown in the drawing.

However, in practice, light signals may be measured from not only a reference pixel but also other pixels as shown in FIG. 8 because of such factors as that electrodes of respective pixels are somewhat away from the position where light signals generate electrons.

Therefore, in the present disclosure, it is possible to appropriately compensate for such crosstalk according to the algorithm described below to accurately measure a spectrum.

Hereinafter, the algorithm used for crosstalk correction will be explained. Assuming that crosstalk occurs in three adjacent pixels and all the pixels undergo the same crosstalk, the spectrometer performs crosstalk correction according to the following equations.

$$y[1] = a0\,x[1] + a1\,x[2] + a2\,x[3] + a3\,x[4]$$

$$y[2] = a1\,x[1] + a0\,x[2] + a1\,x[3] + a2\,x[4] + a3\,x[5]$$

$$y[3] = a2\,x[1] + a1\,x[2] + a0\,x[3] + a1\,x[4] + a2\,x[5] + a3\,x[6]$$

$$y[4] = a3\,x[1] + a2\,x[2] + a1\,x[3] + a0\,x[4] + a1\,x[5] + a2\,x[6] + a3\,x[7]$$

$$\ldots$$

$$y[n] = a3\,x[n-3] + a2\,x[n-2] + a1\,x[n-1] +$$
$$a0\,x[n] + a1\,x[n+1] + a2\,x[n+2] + a3\,x[n+3]$$

$$\ldots$$

$$y[N-3] = a3\,x[N-6] + a2\,x[N-5] +$$
$$a1\,x[N-4] + a0\,x[N-3] + a1\,x[N-2] + a2\,x[N-1] + a3\,x[N]$$

$$y[N-2] = a3\,x[N-5] + a2\,x[N-4] +$$
$$a1\,x[N-3] + a0\,x[N-2] + a1\,x[N-1] + a2\,x[N]$$

$$y[N-1] = a3\,x[N-4] + a2\,x[N-3] +$$
$$a1\,x[N-2] + a0\,x[N-1] + a1\,x[N]$$

$$y[N] = a3\,x[N-3] + a2\,x[N-2] + a1\,x[N-1] + a0\,x[N],$$

where x[n]: ideal value supposed to be measured from an nth pixel y[n]: Value actually measured from the nth pixel a0: Ratio of a value actually measured from one pixel to an ideal value supposed to be measured from that pixel a1: Ratio of a value actually measured from a first adjacent pixel to an ideal value supposed to be measured from one pixel a2: Ratio of a value actually measured from a second adjacent pixel to an ideal value supposed to be measured from one pixel a3: Ratio of a value actually measured from a third adjacent pixel to an ideal value supposed to be measured from one pixel N: Number of pixels The above-described equations can be arranged in a matrix form, and, thus, the following matrix equations can be produced.

$$Y = [y[1]\,y[2]\,\ldots\,y[N]]'$$

$$X = [x[1]\,x[2]\,\ldots\,x[N]]'$$

$$\ldots$$

$$A = \begin{pmatrix} \alpha_0 & \alpha_1 & \alpha_2 & \alpha_3 & 0 & 0 & 0 & 0 & 0 & 0 & 0 & 0 & 0 & 0 & 0 \\ \alpha_1 & \alpha_0 & \alpha_1 & \alpha_2 & \alpha_3 & 0 & 0 & 0 & 0 & 0 & 0 & 0 & 0 & 0 & 0 \\ \alpha_2 & \alpha_1 & \alpha_0 & \alpha_1 & \alpha_2 & \alpha_3 & 0 & 0 & 0 & 0 & 0 & 0 & 0 & 0 & 0 \\ \alpha_3 & \alpha_2 & \alpha_1 & \alpha_0 & \alpha_1 & \alpha_2 & \alpha_3 & 0 & 0 & 0 & 0 & 0 & 0 & 0 & 0 \\ 0 & \alpha_3 & \alpha_2 & \alpha_1 & \alpha_0 & \alpha_1 & \alpha_2 & \alpha_3 & 0 & 0 & 0 & 0 & 0 & 0 & 0 \\ . & . & . & . & . & . & . & . & . & . & . & . & . & . & 0 \\ 0 & . & . & . & \alpha_3 & \alpha_2 & \alpha_1 & \alpha_0 & \alpha_1 & \alpha_2 & \alpha_3 & . & . & . & 0 \\ . & . & . & . & . & . & . & . & . & . & . & . & . & . & . \\ 0 & 0 & 0 & 0 & 0 & 0 & 0 & \alpha_3 & \alpha_2 & \alpha_1 & \alpha_0 & \alpha_1 & \alpha_2 & \alpha_3 & 0 \\ 0 & 0 & 0 & 0 & 0 & 0 & 0 & 0 & \alpha_3 & \alpha_2 & \alpha_1 & \alpha_0 & \alpha_1 & \alpha_2 & \alpha_3 \\ 0 & 0 & 0 & 0 & 0 & 0 & 0 & 0 & 0 & \alpha_3 & \alpha_2 & \alpha_1 & \alpha_0 & \alpha_1 & \alpha_2 \\ 0 & 0 & 0 & 0 & 0 & 0 & 0 & 0 & 0 & 0 & \alpha_3 & \alpha_2 & \alpha_1 & \alpha_0 & \alpha_1 \\ 0 & 0 & 0 & 0 & 0 & 0 & 0 & 0 & 0 & 0 & 0 & \alpha_3 & \alpha_2 & \alpha_1 & \alpha_0 \end{pmatrix}$$

Finally, the equation "Y=AX" is produced from the above matrix equations, and the following formula can be used to perform the crosstalk correction from values actually measured.

$$\text{"}X = A^{-1}Y\text{"}$$

In this case, although seven factors were used in the above matrix equations, three or five factors may be used for simplifying the matrix equations or nine or more factors may be used for refining the matrix equations. Also, much more factors may be used if the crosstalk occurs differently in each pixel. That is, after factors are determined in advance through measurement of the sensor, the factors are stored in a storage medium to form a matrix equation and the inverse matrix is also calculated in real time to perform crosstalk correction.

Further, in an optional embodiment, an equation for crosstalk correction may be simplified. This is because a complicated equation may cause slowdown in the computing speed of the spectrometer. Therefore, significant factors of an inverse matrix corresponding to a matrix equation are stored in advance, and, thus, a simplified equation using only addition and multiplication can be applied.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A compact handheld optical coherence tomography (OCT) spectrometer, comprising:
    a spectrometer optical module;
    a sensor board coupled to one side of the spectrometer optical module and equipped with a sensor that converts light received from the spectrometer optical module into an electrical signal; and
    a connector configured to supply, to the sensor board, a control signal and a power signal from the connector received from another circuit outside the spectrometer and to transmit a signal received from the sensor board to another external circuit,
    wherein the sensor board is packaged with the spectrometer optical module, and
    the sensor is formed to be exposed from a surface of the sensor board, and a light receiving portion of the sensor is configured to face the inside of the packaged component and collect light from the spectrometer optical module.

2. The compact handheld OCT spectrometer of claim 1, wherein the sensor is manufactured to be embedded in the sensor board without going through its own packaging process.

3. The compact handheld OCT spectrometer of claim 1, wherein a cover glass is not provided on top of the light receiving portion of the sensor.

4. The compact handheld OCT spectrometer of claim 1, wherein each of a plurality of pixels forming the sensor has a width of less than 10 μm.

5. The compact handheld OCT spectrometer of claim 1, wherein the sensor is configured as a low-power circuit to operate with a predetermined input power.

6. The compact handheld OCT spectrometer of claim 4, wherein the deterioration of optical detection sensitivity is minimized by designing a size of the focus of each wavelength component of a light signal received by the sensor to be smaller than the width of the pixel.

7. The compact handheld OCT spectrometer of claim 1, wherein the sensor board is equipped with a voltage conversion unit, so that if the sensor board does not receive a predetermined voltage from the connector, the voltage conversion unit converts the power signal from the connector into another voltage level required for power supply.

8. The compact handheld OCT spectrometer of claim 1, wherein the sensor board further includes an analog-to-digital converter that converts an analog signal received from the sensor into a digital signal and transmits the digital signal to the connector, and
    the analog-to-digital converter has a voltage range of the input analog signal level from a noise floor to a voltage level corresponding to a full well capacity of the sensor, and
    the full well capacity refers to the maximum number of electrons accumulated for a predetermined period of time in each pixel inside the sensor after the pixel receives light.

9. The compact handheld OCT spectrometer of claim 1, wherein the connector transmits the digital signal generated by an analog-to-digital converter to a main board outside the spectrometer.

10. The compact handheld OCT spectrometer of claim 1, further comprising:
    a correction module configured to perform correction to an electrical signal value measured from each of a plurality of pixels of the sensor,
    wherein the correction module performs the correction to reduce at least one differences in electrical signal values among the pixels caused by different photoelectric conversion characteristic values among the pixels and reduce at least one differences in noise floor characteristic values among the pixels when light is not incoming.

11. The compact handheld OCT spectrometer of claim 10, wherein the correction module performs the correction by subtracting a factor reflecting different offset values of respective pixels from the electrical signal values measured from those respective pixels and dividing the resulting values by the factor reflecting different gain values of the respective pixels for identical input light levels.

12. The compact handheld OCT spectrometer of claim 10, wherein in order to correct crosstalk of an optical sensor of the spectrometer, the correction module produces an equation by using ratios of electrical signal values actually measured from adjacent pixels after crosstalk to an ideal electrical signal value supposed to be measured when a light signal is incident to a single pixel, electrical signal values actually measured from the respective pixels when the spectrometer is actually operated and an electrical signal value in an ideal state without crosstalk, and
    the electrical signal values measured from the respective pixels are corrected according to the produced equation.

13. The compact handheld OCT spectrometer of claim 10, wherein in order to correct nonlinearity of the electrical signal value to the light signal incident to the pixel, the correction module performs the correction by in advance generating a function or a lookup table where a nonlinear electrical signal value and an ideal linear electrical signal value corresponding to the same light signal in a nonlinear region are respectively produced and matched to each other and by calculating the linear electrical signal value based on the function or the lookup table when the spectrometer actually measures the light signal and receives the nonlinear electrical signal value.

* * * * *